United States Patent [19]

Bergersen

[11] Patent Number: 4,881,896
[45] Date of Patent: Nov. 21, 1989

[54] MUSCULAR EXPANSION BUMPER AND HEAD-GEAR APPLIANCE

[76] Inventor: Earl O. Bergersen, 950 Green Bay Rd., Winnetka, Ill. 60093

[21] Appl. No.: 255,963

[22] Filed: Oct. 11, 1988

Related U.S. Application Data

[63] Continuation-in-part of Ser. No. 109,938, Oct. 19, 1987, Pat. No. 4,797,093.

[51] Int. Cl.[4] .................................................. A61C 7/00
[52] U.S. Cl. ............................................. 433/5; 433/7
[58] Field of Search ...................................... 433/5, 6, 7

[56] References Cited

U.S. PATENT DOCUMENTS 4,330,272  5/1982  Bergersen ................................. 433/5
4,637,796  1/1987  Korn ........................................ 433/7

Primary Examiner—Robert Peshock
Attorney, Agent, or Firm—Hill, Van Santen, Steadman & Simpson

[57] ABSTRACT

A muscular expansion bumper appliance is optionally removable from a patient's mouth and includes a wire form member formed in a U-shape with the free ends which may be removably secured to buccal tubes. The wire form member supports at least one side pad which overlies one or both of the upper or lower posterior teeth to hold the user's cheeks away from those teeth to permit lateral posterior expansion. The side pads are formed by plate members secured to the wire form member covered with a plastic material. The plastic material can be trimmed to custom fit the appliance to the user and the appliance comes in varying sizes.

18 Claims, 3 Drawing Sheets

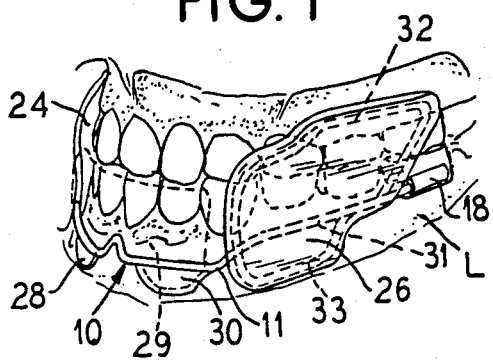
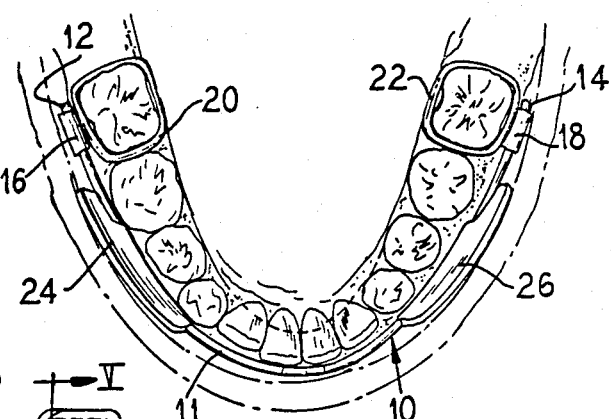
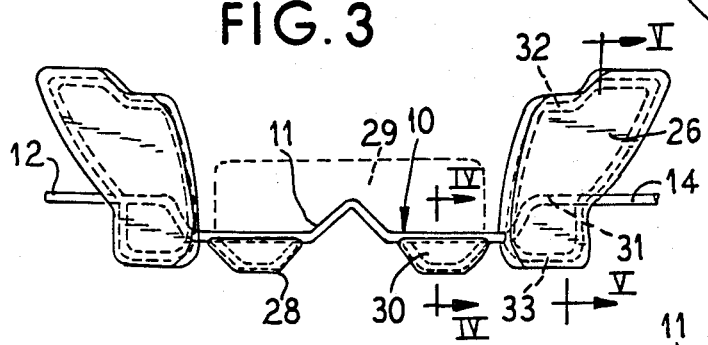
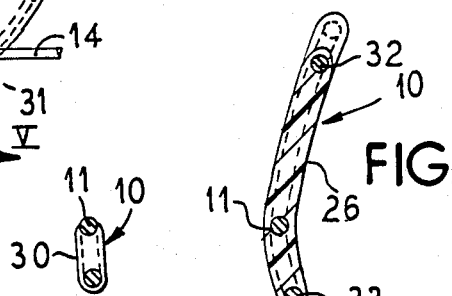
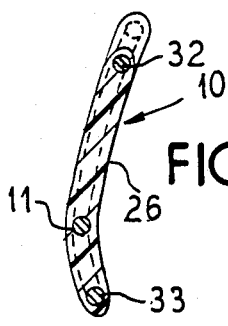
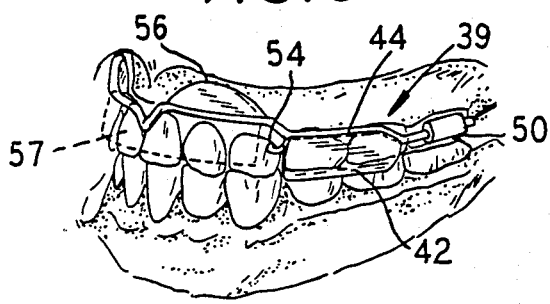
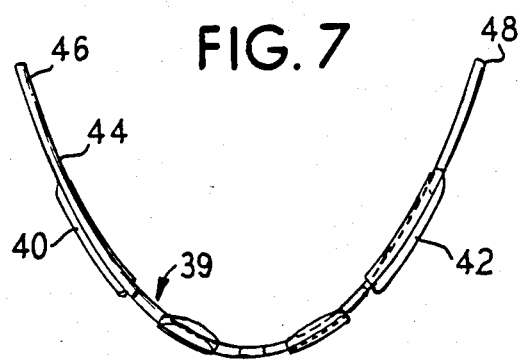
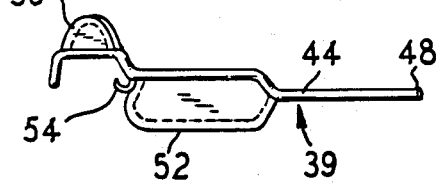
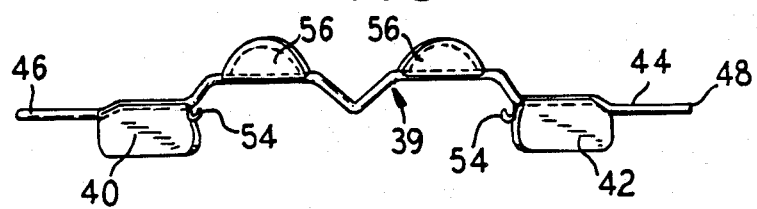

U.S. Patent  Nov. 21, 1989  Sheet 3 of 3  4,881,896
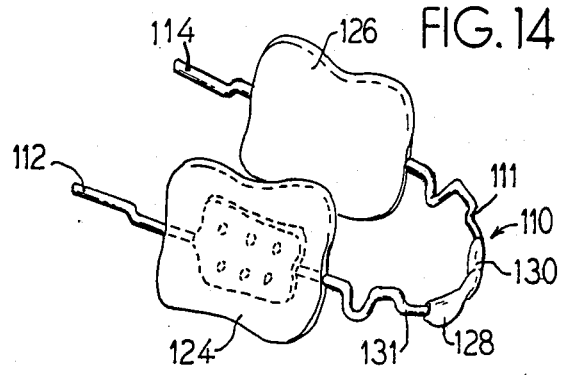
FIG. 14
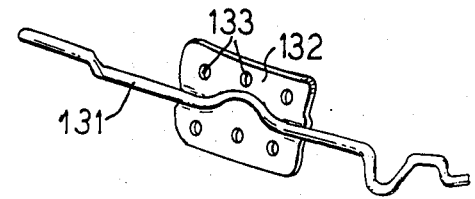
FIG. 15
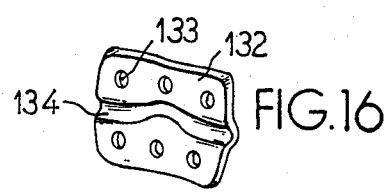
FIG. 16
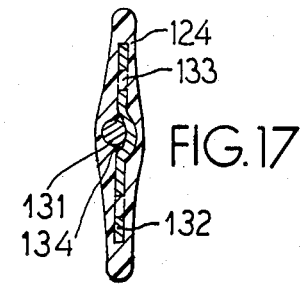
FIG. 17
FIG. 19
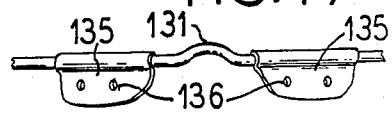
FIG. 18
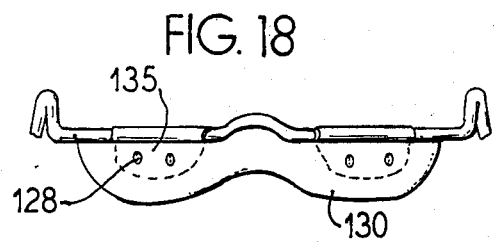
FIG. 20
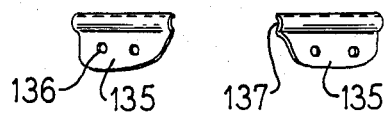
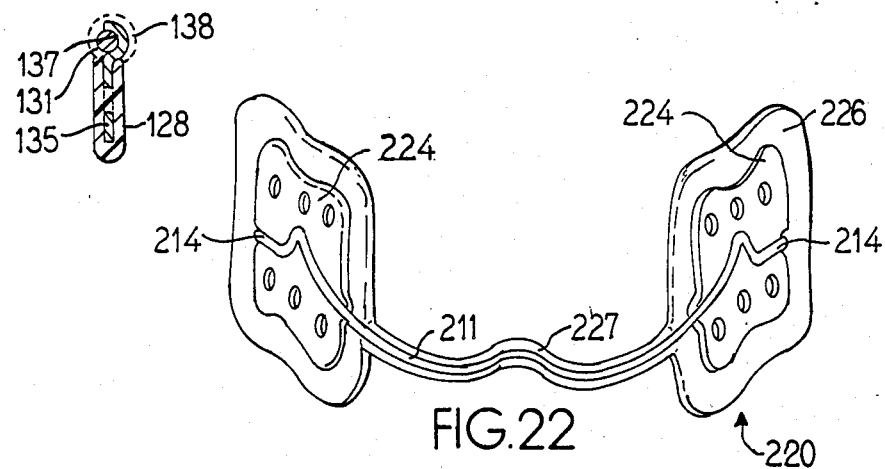
FIG. 21
FIG. 22

MUSCULAR EXPANSION BUMPER AND HEAD-GEAR APPLIANCE

This application is a continuation-in-part application of Ser. No. 109,938 filed on Oct. 19, 1987 and now Pat. No. 4,797,093 issued Jan. 10, 1984.

BACKGROUND OF THE INVENTION

1. Field of the Invention

The present invention relates to orthodontic appliances and more particularly to an appliance for providing lateral expansion of the upper and/or lower posterior segments.

2. Description of the Prior Art

Frequently there is a lack of room for the front (especially lower) permanent incisors when they first erupt into the mouth at 7-9 years of age. This lack of room is frequently anteriorly across the front of the lower jaw because the permanent incisors are considerably larger than the deciduous teeth that preceded them. If the lack of space is not corrected prior to the eruption of these permanent teeth, they rotate and are displaced out of position upon their eruption. The collagenous fibers then gradually form and hold them in their rotated and crowded position. If the teeth are eventually straightened, even with creation of additional space by whatever means, they frequently rotate back toward their original crowded and rotated positions. When similar teeth are straightened as they erupt at 7 or 8 years of age or shortly after, they tend to stay straight probably due to the collagenous fibers that are formed around these teeth after they were straightened. Since the erupting teeth were not allowed to become rotated and crowded and allowed to stay that way, the fibers were never formed originally in the rotated or crowded position. Therefore, it would be preferable to provide expansion at an early age, before the eruption of the lower permanent incisors at about from a very early age up to about 8 years of age as a form of preventive type orthodontic treatment. Or it can be done later or at any age when it seems appropriate to get expansion of the arches.

A drawback to expanding both the upper and lower posterior segments at the same time is that usually if one arch is expanded, the opposite arch must be expanded with another appliance which results in a mouth full of double appliance and is twice the appliance cost. A custom-made removable-type appliance known in the art as the "Frankel" has been used for expansion on the sides, but this requires that the user, generally a young child, keep the appliance in the mouth for a sufficient amount of time to provide the required effect. As can be expected, voluntary usage of such a device oftentimes leads to less than satisfactory results.

SUMMARY OF THE INVENTION

The present invention provides a single device which can be preformed and can be a fixed type of appliance utilized on a bumper, therefore being removable only by a dentist or also by the patient if required or in an emergency. The invention also encompasses a single device which can be preformed and which is readily removable by the patient. The entire appliance can be preformed or can be supplied as a metal form to be custom-made to add side pads or front pads as needed, used for the expansion as a custom-fit to a model of the mouth. The bumper embodying the principles of the present invention is used to provide lateral expansion of the upper posterior segments or the lower posterior segments or both at the same time through the use of a single appliance or expansion in the front section by increasing the pad size in front. If expansion is required across the upper front, the appliance is made to fit into upper molar bands the same way that it fits in the lower. The expansion bumper can be designed to fit into buccal tubes on the first or second permanent molars or to the second deciduous molars on either the upper or lower arch.

The appliance is designed on the side of the posterior region to hold a plastic shield that can be molded around the wire support. The wire support can take various shapes as an all in one bent wire or a soldered addition. Additionally, a plate can be permanently attached to the wire form such as by welding or soldering to hold the plastic shield. The added soft pliable plastic will allow the pads to be adapted to the mouth to avoid soft-tissue impingement by bending the inside wire or plate and the plastic will deform along with the wire or plate. Or the plastic can be of the type that is either hard or pliable at the mouth temperature but can be remoldable with an increase in the temperature or can be of a self curing acrylic or any other moldable plastic or rubber silicon material or pliable or hard moldable material. If the plate is utilized, it can be bent into a desired position and will stay in that bent position and not be deformed gradually by the elevated temperature in the mouth.

This appliance can be made in various sizes to fit various sized mouths, that is for example small, medium and large or as many as necessary to enable the appliance to function in the mouth when chewing, etc., without getting sore spots or being uncomfortable. It can also be made for the deciduous dentition, mixed dentition or adult dentition.

The present appliance provides advantages over devices previously utilized in its ability to expand the posterior segments in a lateral direction as it is driving the molars distally and can also move the front teeth forward all at the same time while being used in the mouth. Also, since it is able to expand both the upper and lower posterior segments at the same time with a single appliance, drawbacks of having excessive numbers or amounts of appliances in the mouth is avoided. As mentioned, the appliance can be fixed within the mouth by attachment to the buccal tubes or can be utilized with a head gear to provide additional distal drive to the molars, or added to any form of head-gear device when not actually secured to the posterior teeth.

BRIEF DESCRIPTION OF THE DRAWINGS

FIG. 1 is a perspective view of an expansion bumper incorporating the principles of the present invention.

FIG. 2 is an occlusal view of the lower arch illustrating the expansion bumper of FIG. 1.

FIG. 3 is an anterior view of the expansion bumper of FIG. 1 alone.

FIG. 4 is a sectional view taken generally along the line IV—IV of FIG. 3.

FIG. 5 is a sectional view taken generally along the line V—V of FIG. 3.

FIG. 6 is a perspective view of an expansion bumper incorporating the principles of the present invention attached to the upper arch.

FIG. 7 is a top view of the bumper of FIG. 6 shown alone.

FIG. 8 is a buccal view of the expansion bumper of FIG. 7.

FIG. 9 is an anterior view of the bumper of FIG. 7.

FIG. 14 is a perspective view of an expansion bumper incorporating the principles of the present invention utilizing an anterior plate.

FIG. 15 is a side elevational view of a portion of the bumper of FIG. 1 with the plastic shield removed.

FIG. 16 is a side elevational view of the plate by itself.

FIG. 17 is a side sectional view of the side plate of FIG. 14.

FIG. 18 is a front elevational view of a portion of the bumper showing the bumper pads.

FIG. 19 is a front elevational view of the bumper pad area with the plastic removed.

FIG. 20 is a front elevational view of the front plate for the bumper pad by itself.

FIG. 21 is a side sectional view through the front bumper pad of FIG. 18.

FIG. 22 is a perspective view of an alternative embodiment of a removable appliance incorporating the principles of the present invention.

DESCRIPTION OF THE PREFERRED EMBODIMENTS

Figure 10:
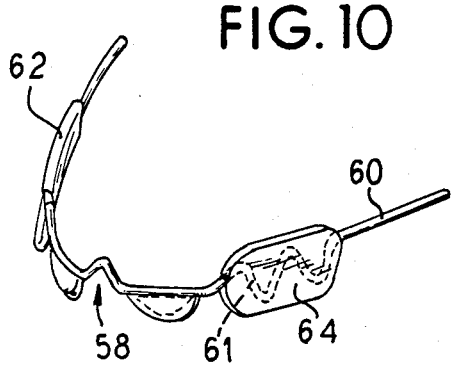
FIG. 10 is a perspective view of an expansion bumper incorporating the principles of the present invention having a differing interior wire form.

The present invention provides a bumper where individual lateral expansion of the upper posterior segments (FIGS. 6-9), or of the lower posterior segments (FIGS. 10-11), or of both at the same time (FIGS. 1-5, 12-14 and 22) can be performed, or of the anterior segment of upper (FIG. 6 in phantom) or lower (FIGS. 1 and 3 in phantom and FIG. 18) as well.

In FIGS. 1-5 there is illustrated a muscular expansion bumper generally at 10 which, although secured to a lower arch L, can be used to provide expansion of both the upper posterior segment as well as the lower posterior segment. The bumper is formed in a generally U-shaped configuration as seen in FIG. 2 with a wire form member 11. Free ends 12, 14 of the U-shaped configuration being a single projecting wire, each of which is to be received in a buccal tube 16, 18 secured to a molar band 20, 22 held on the first permanent molar as illustrated in FIG. 2. The band can also be attached to the second permanent molar or second deciduous molar depending on the patient's stage of dentition, or any other tooth or instead of a band, the tube can be directly bonded to the enamel of the tooth without having a band around the tooth.

The bumper includes two lateral side pads 24, 26 formed from a resilient plastic material which extend superiorly and inferiorly of the wire form member 11 from a posterior position close to the free end of the U-shaped frame that is secured in the buccal tubes to an anterior position so as to overlie the buccal sides of the molars, premolars or bicuspids, and canines.

The wire form member 11, which is attached solely at its free ends 12, 14 to the molars, is spaced away from the teeth which it overlies to remove the buccal and labial pressure normally applied to the teeth so as to permit lateral expansion, particularly in the posterior segment from the action of the tongue. The band also includes anterior pads 28, 30 to hold the lower lip away from the lower incisors to permit expansion in that area and to provide distal pressure on the anchoring molar. These front pads 28, 30 can be positioned low only for anchorage or high as illustrated in phantom at 29 for labial tooth movement, or both high and low for both functions.

The wire from member 11 is shown in FIGS. 1-5 as being comprised of a single continuous wire 31 having the general U-shape with added wire segments extending superiorly 32 and inferiorly 33 of the continuous wire 31 to provide an increased area support for the pads. The pads themselves are molded onto the wire form and wire segments and are contoured in a vertical direction such that they curve in a buccal direction from the continuous wire form portion to hold the cheeks sufficiently away from the teeth so as to permit the desired expansion. The use of the wire segments permits an add on of side pads of various dimensions to extend or diminish the function or effect of these pads on the wire. The extensions can be in separate pieces so to be soldered in place by a custom finisher, or can be in one wire configuration for easier molding. In a lab or dentist hand-made adaptation setting, the shield could be acrylic (self cure or cureable) instead of injection molded. Also, the pads extend outwardly beyond the added wire segments 32, 33 to form a peripheral margin area which may be selectively trimmed by the dentist to provide a custom fit of the pads.

FIGS. 6-9 illustrate an appliance 39, similar to that illustrated in FIGS. 1-5, but the appliance in FIGS. 6-9 is attached to the upper molars and includes side pads 40, 42 to overlie only the upper bicuspids to provide lateral expansion of only the upper posterior segments. Again, the appliance is comprised of a continuous U-shaped wire form member 44 having free posterior ends 46, 48 which are received in buccal tubes 50 secured to the upper molars. A wire addition 52 is soldered to the wire form member 44 to provide an increased support shape for the side pads 40, 42. As is common in appliances used in the mouth, hooks 54 for receiving elastic bands may also be attached to the wire frame 44. Upper labial pads 56 are also provided on the appliance of FIGS. 6-9 to hold the upper lip away from the upper incisors and to provide distal pressure to the anchoring molars.

Figure 11:
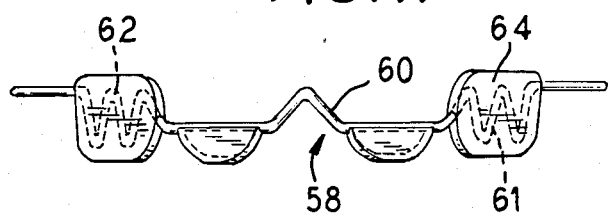
FIG. 11 is an anterior view of the bumper of FIG. 10.

FIGS. 10 and 11 illustrate an appliance 58 which can be used for providing lateral expansion of only the lower posterior segment in which a single continuous wire form member 60 is formed in a U-shape as seen from above and which includes a serpentine configuration 61 or W-shape in the region where buccal side pads 62, 64 are molded on the wire form member 60. In all other respects, the form of the appliance 58 is substantially similar to appliance 39 of FIGS. 6-9, except of course that appliance 58 is to be used for lower lateral expansion and appliance 39 is to be used for upper lateral expansion.

Figure 12:
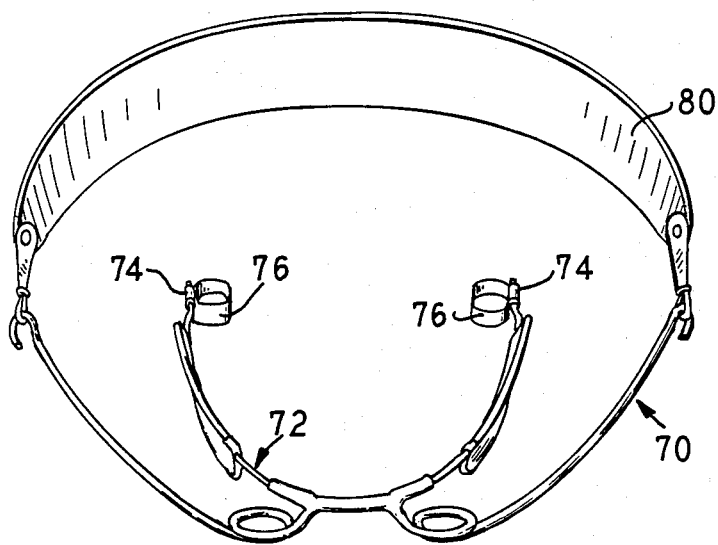
FIG. 12 is a top perspective view of an expansion bumper incorporating the principles of the present invention and utilized with a head gear.
Figure 13:
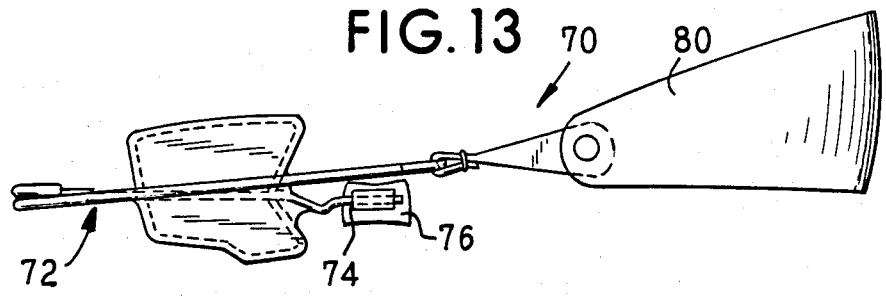
FIG. 13 is a buccal elevational view of the head gear appliance of FIG. 12.

FIGS. 12 and 13 illustrate a head gear appliance 70 which includes a muscular expansion bumper 72 incorporating the principles of the present invention as described above. The expansion bumper 72 is substantially identical to the embodiment illustrated in FIGS. 1-5 in that it is used for lateral expansion of the upper posterior segments and lower posterior segments at the same time and is secured to buccal tubes 74 on molar bands 76 positioned on the upper or lower molars. Since the head gear appliance includes a strap 80 which encircles the user's head to provide the distal drive to the molars, the anterior labial pads illustrated in FIGS. 1–3 are not required but can be used if labial movement of upper incisors is required or alveolar bone apposition is needed or if additional distal movement of molars is desired.

FIG. 14 illustrates another embodiment of a muscular expansion bumper generally at 110 which, similar to the expansion bumper 10 described above can be used to provide expansion of both the upper posterior segment as well as the lower posterior segment and the upper and lower anterior segments. The bumper 110 is formed in a generally U-shaped configuration with a wire form member 111. Free ends 112, 114 of the U-shaped configuration being a single projecting wire, each of which is to be received in a buccal tube as described above.

The bumper 110 includes two lateral side pads 124, 126 formed from a resilient plastic material which extends superiorly and inferiorly of the wire form member 111 from a posterior position close to the free end of the U-shaped frame to an anterior position so as to overlie the buccal sides of the molars, premolars or bicuspids, and canines. As described above, the wire form member 111 is spaced away from the teeth which it overlies to remove the buccal and labial pressure normally applied to the teeth so as to permit lateral expansion, particularly in the posterior segment from the action of the tongue. The wire form member also includes anterior pads 128, 130 to hold the lower lip away from the lower incisors to permit expansion in that area and to provide distal pressure on the anchoring molar. These front pads 128, 130 can be positioned low only for anchorage or high for labial tooth movement, or both high and low for both functions.

The wire form member 111 is comprised of a single continuous wire 131 having the general U-shape with added plate members 132 extending superiorly and inferiorly of the continuous wire 131 to provide an increased area support for the pads 124, 126. The plate members 132 are secured to the wire 131 by appropriate means such as welding or soldering. The pads themselves comprise a soft plastic material which is molded onto the plate member 132. The plate member includes means for enhancing the adherence of the plastic on the plates comprising a plurality of apertures 133 extending therethrough to provide an anchoring for the plastic molded onto the plates 132. The plate member 132 also includes a means for enhancing the securement of the plate to the wire 131 comprising a channel or groove 134 formed in the plate by bending the plate, the channel designed to receive the continuous wire 131, preferably in a serpentine or bent fashion along the length of the channel so that there is resistance to axial movement of the plate on the wire. The plate, which preferably can be formed of a thin piece of stainless steel or a nickel alloy is welded or soldered or by some other means permanently affixed to the wire so as to prevent any movement between the wire and the plate. By attaching the wire within a groove on the plate and by forming the groove in a non-linear shape, permanent securing of the plate to the wire is enhanced.

The plates are contoured in a vertical direction such that they curve in a buccal direction from the continuous wire form portion to hold the cheeks sufficiently away from the teeth so as to permit the desired expansion. The pads themselves are molded onto the plates and follow the contour of the plates. The use of the plates permits an add-on of side pads of various dimensions to extend or diminish the function or effect of these pads on the wire. The pads extend outwardly beyond the edge of the plates to form a peripheral margin area which may be selectively trimmed by a dentist to provide a custom fit for the pads.

As seen in FIGS. 18–21, plates 135 having apertures 136 and formed channels or grooves 137 can be provided at the anterior portion of the bumper and can also be permanently secured to the wire 131 as described above. The plastic covering of the plates 135 may or may not extend over the top of the wire, as desired and as illustrated in phantom at 138 in FIG. 21.

An alternative embodiment of a bumper is shown generally at 210 in FIG. 22 and is similar to the bumper 110 described above in that the bumper 210 is formed in a generally U-shaped configuration with a wire form member 211. However, ends 212, 214 of the wire form member are secured to plate members 224 and do not extend beyond a rearward edge of the plate member. Thus, the appliance is not permanently attached within the mouth, but can be easily and readily removed and reinserted by the patient. In all other respects, the bumper 220 may be substantially identical to that shown in FIG. 14, with the exception that there are no anterior pads on bumper 220 although such pads could be added if desired. A further enhancement is illustrated in FIG. 22 in that the wire form member 211 has a coating of plastic 227 along its entire length to provide a cushioning of the wire against tissue surfaces within the mouth.

Thus, it is seen that the present invention provides an appliance which effects lateral expansion of the upper and lower posterior segments alone or at the same time, the appliance being fixed within the user's mouth so that treatment is not dependent upon voluntary participation by the user which generally is a child, thereby increasing the effectiveness of the appliance. In some applications it could be removable from the bands. Further, the appliance provides the expansion, and particularly combined upper and lower expansion with a minimal amount of hardware to be placed in the user's mouth. It can also provide anterior expansion as well with pads placed at varying levels in the front of the mouth.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A muscular expansion bumper appliance for use in correcting human dentition comprising:
   a wire form member having a generally U-shaped configuration having a central bight portion with two free posterior ends;
   at least one metallic plate member secured to said wire form member and extending vertically at least one of superior to or inferior to said wire form member;
   said metallic plate member positioned on said wire form member between said free ends and said central bight portion; and a plastic material covering said metallic plate member.

2. A muscular expansion bumper appliance according to claim 1, wherein there are a plurality of plate members which extend both superior to and inferior to said wire form member.

3. A muscular expansion bumper appliance according to claim 1, wherein said plate member is formed from a bendable material.

4. A muscular expansion bumper appliance according to claim 1, wherein one plate member is provided on each lateral side of said wire form member.

5. A muscular expansion bumper appliance according to claim 1, wherein said plate member has a channel formed therein for receiving a portion of said wire form member.

6. A muscular expansion bumper appliance according to claim 1, wherein said plastic covering extends over the entire exterior surface of said plate member.

7. A muscular expansion bumper appliance according to claim 1, wherein said plastic covering extends beyond said plate member to permit portions of said pad to be trimmed to custom fit the appliance to the user.

8. A muscular expansion bumper appliance according to claim 5, wherein said wire form member has a serpentine configuration in the region of its securement to said plate member and said channel has a corresponding serpentine configuration such that said wire form member is prevented from moving axially relative to said plate member.

9. A muscular expansion bumper according to claim 4, wherein said two free posterior ends of said wire form member terminate in points of attachment to said plate members.

10. A muscular expansion bumper according to claim 1, wherein said two free posterior ends of said wire form member extend beyond said plate member.

11. A muscular expansion bumper appliance for use in providing posterior lateral expansion of human dentition comprising:
 a wire form member having a generally U-shaped configuration with two free posterior ends, said ends being removably secured in buccal tubes for attachment a user's molars;
 at least one metallic plate member secured to said wire form member to overlie the buccal side of at least one of the upper or lower posterior teeth of the user, and
 a plastic covering molded over said metallic plate member,
whereby, the user's cheeks will be held away from the adjoining teeth to permit posterior lateral expansion to occur.

12. A muscular expansion bumper appliance according to claim 11, wherein said plate member overlies both upper and lower teeth.

13. A muscular expansion bumper appliance according to claim 11, wherein said metallic plate member is formed from a bendable material.

14. A muscular expansion bumper appliance according to claim 11, including means formed on said plate member to enhance adherence of said plastic to said plate member.

15. A muscular expansion bumper appliance according to claim 11, wherein said means to enhance adherence comprises at least one aperture through said plate member.

16. A muscular expansion bumper appliance according to claim 11, including means formed on said plate member to enhance securement of said plate member to said wire form member.

17. A muscular expansion bumper appliance according to claim 16, wherein said means to enhance securement comprises a channel formed in said plate member to receive said wire form member.

18. A muscular expansion bumper appliance according to claim 17, wherein said wire form member has a serpentine configuration in the region of its securement to said plate member and said channel has a corresponding serpentine configuration such that said wire form member is prevented from moving axially relative to said plate member.

* * * * *